United States Patent [19]

Meybeck et al.

[11] Patent Number: 5,476,651

[45] Date of Patent: Dec. 19, 1995

[54] COSMETIC OR PHARMACEUTICAL COMPOSITION, ESPECIALLY DERMATOLOGICAL COMPOSITION, INTENDED FOR PROMOTING THE PIGMENTATION OF THE SKIN OR HAIR, CONTAINING AN EXTRACT OF CYPERUS, AND THE PROCESS FOR ITS MANUFACTURE

[75] Inventors: Alain Meybeck; Frédéric Bonte, both of Courbevoie; Marc Dumas, Colombes, all of France

[73] Assignee: LVMH Recherche, Colombes, France

[21] Appl. No.: 142,423

[22] PCT Filed: May 19, 1992

[86] PCT No.: PCT/FR92/00444

§ 371 Date: Apr. 22, 1994

§ 102(e) Date: Apr. 22, 1994

[87] PCT Pub. No.: WO92/20322

PCT Pub. Date: Nov. 26, 1992

[30] Foreign Application Priority Data

May 22, 1992 [FR] France ................................. 91 06176

[51] Int. Cl.[6] ................. A61K 7/13; A61K 7/42
[52] U.S. Cl. ................. 424/59; 424/74; 424/195.1
[58] Field of Search .................... 424/195.1, 59, 424/74

[56] References Cited

U.S. PATENT DOCUMENTS

| 4,390,532 | 6/1983 | Stuttgen | 424/240 |
| 5,081,151 | 1/1992 | Davies | 514/574 |

FOREIGN PATENT DOCUMENTS

| 62212319 | 9/1987 | Japan. |
| 62234006 | 10/1987 | Japan. |
| 2048515 | 5/1990 | Japan. |

*Primary Examiner*—C. Warren Ivy
*Assistant Examiner*—Evelyn Huang
*Attorney, Agent, or Firm*—Jacobson, Price, Holman & Stern

[57] ABSTRACT

The invention relates to the use of an extract of Cyperus, in particular *Cyperus rotundus L.* for the preparation of a cosmetic or pharmaceutical composition, especially dermatological composition, intended for promoting the pigmentation of the skin or hair and/or for treating pigmentation disorders.

22 Claims, No Drawings

COSMETIC OR PHARMACEUTICAL COMPOSITION, ESPECIALLY DERMATOLOGICAL COMPOSITION, INTENDED FOR PROMOTING THE PIGMENTATION OF THE SKIN OR HAIR, CONTAINING AN EXTRACT OF CYPERUS, AND THE PROCESS FOR ITS MANUFACTURE

This application is the National Phase of PCT/FR92/ 00444 filed on May 19, 1992.

The present invention relates essentially to a cosmetic or pharmaceutical composition, especially dermatological composition, containing an extract of Cyperus, intended in particular for promoting the pigmentation of the skin or hair, and to the process for its manufacture.

It further relates to the use of an extract of Cyperus for the preparation of such a cosmetic or pharmaceutical composition.

The various species of the genus Cyperus form part of the Cyperaceae family. There are about 650 of these species dispersed throughout the old and new world, with the exception of cold regions. The species of this genus can be determined by reference to Flore complete portative (Pocketbook of Complete Flora) by Gaston Bonnier and G. de Layens, pp. 323 and 324. The Cyperus, also called sedge in English, are annual or perennial herbaceous plants. They generally possess rhizomes. Some also possess tubers. Among the latter, there may be mentioned *Cyperus aureus* or tuberous sedge, *Cyperus esculentus, Cyperus olivaris* or *Cyperus rotundus L.*, which are found particularly in France in sandy locations along part of the mediterranean shore. The tubers of *Cyperus olivaris* or rotundus have been used to treat stomach, lung and bladder diseases. They formed part of the composition of various pharmaceutical preparations such as scorpion oil and theriacal water, which are no longer employed today.

It is also known from the document JP-A-62- 234006 that extracts of tubers of *Cyperus rotundus* have an antiinflammatory activity and can be used for the manufacture of topical cosmetic or pharmaceutical compositions for external application.

Furthermore, it is known from the document U.S. Pat. No. 4,908,207 that extracts of tubers of the plant *Cyperus rotundus L.*, administered orally, can be used to treat immune deficiencies.

It is also known from the document U.S. Pat. No. 4,696,818 that courses of detoxication treatment can be carried out using medicinal compositions containing especially *Cyperus rotundus* in combination with other plant extracts, particularly extracts of roots of *Angelica sinensis*.

In addition, the document U.S. Pat. No. 4,826,684 has disclosed a pharmaceutical composition containing a mixture of terpenoids derived from an extract of the tubers of the plant *Cyperus rotondus L.*, which is administered orally for the treatment of diabetes.

The present invention is based on the discovery that extracts of Cyperus, in particular those originating from the rhizomes or tubers, have valuable biological properties which can be utilized in the cosmetic and pharmaceutical fields. In particular, the inventors have observed that these extracts unexpectedly possess a stimulating activity on melanogenesis in the melanocytes present in the skin or the hair follicles, and thus make it possible to promote the pigmentation of the skin or hair as well as to treat disorders of the pigmentation of the skin and hair, more particularly by promoting the biosynthesis of melanin. Very good results in this field have been obtained with extracts of tubers of *Cyperus rotundus L.*

One object of the present invention is therefore to solve the novel technical problem which consists in providing a novel cosmetic or pharmaceutical composition, especially dermatological composition, intended in particular for promoting the pigmentation of the skin or hair.

A further object of the present invention is to solve the novel technical problem which consists in preparing a novel formulation of a cosmetic or pharmaceutical composition having a good stimulating activity on melanogenesis in the melanocytes present in the skin or in the hair follicles.

A further object of the present invention is to provide a solution to the novel technical problem which consists in providing a plant extract which is particularly easy to obtain and which inherently has a good stimulating activity on melanogenesis in the melanocytes present in the skin or the hair follicles, without it being necessary to isolate any kind of active substance, these isolation processes generally being lengthy and expensive.

All these novel technical problems are solved for the first time by the present invention in a satisfactory manner which can be used on the industrial scale.

Thus, according to a first feature, the present invention relates to a cosmetic or pharmaceutical composition, especially dermatological composition, intended for promoting the pigmentation of the skin or hair, said composition comprising an extract of Cyperus as the active ingredient, optionally in a cosmetically or pharmaceutically acceptable excipient.

According to one particular characteristic of the invention, the extract of Cyperus is an extract of rhizomes or tubers. Said extract is advantageously an extract of tubers of *Cyperus rotundus*.

According to another characteristic, an organic extract of Cyperus, in particular of rhizomes or tubers, is used which is advantageously obtained by a process comprising at least one extraction step with a solvent selected from the group consisting of methanol, ethanol or an aqueous-alcoholic mixture of these alcohols, ethyl acetate and dichloromethane. More generally, other solvents which can be used are organic solvents such as aromatic hydrocarbons, halogenated aliphatic or aromatic hydrocarbons, dialkyl ethers, dialkyl ketones, alkanols, carboxylic acids and esters thereof, or other solvents such as dimethylformamide, dioxane, tetrahydrofuran and dimethyl sulfoxide. Preferred solvents among those mentioned above are benzene, toluene or xylene, methylene chloride, chloroform, ethyl acetate, methanol or ethanol. The ratio of plant material to extraction agent is not critical, but it is generally between 1:5 and 1:20 parts by weight and preferably about 1:10. The extraction is carried out at temperatures between room temperature and the boiling point of the solvent used for the extraction. An advantageous extraction technique is the so-called Soxhlet extraction technique. It may be advantageous, and in some cases necessary, to evaporate the solvent off, for example by lyophilization, and to take up the crude extracts for the purpose of purification. In the framework of the present invention, extraction with an alcohol is particularly valuable, especially at the end of the procedure for obtaining the extract, because alcohols usually have a low toxicity. Thus a particularly advantageous alcohol is ethanol or methanol.

In general, the concentration of the extracts used according to the present invention for the preparation of a cosmetic or pharmaceutical composition, expressed by dry weight, is between 0.002% and 5% by weight, preferably between 0.01% and 1% by weight, based on the total weight of the composition.

The cosmetic or pharmaceutical compositions, especially dermatological compositions, according to the present invention can be applied topically in order to promote the pigmentation of the skin and hair, in particular in compositions in the form of creams, gels or lotions intended for application to the skin or hair.

Thus the cosmetic or pharmaceutical compositions, especially dermatological compositions, according to the invention have a variety of applications in cosmetology or dermatology, in particular where it is desired to enhance the pigmentation. For example, these compositions can be used as sun products to accelerate or intensify tanning, which, apart from the esthetic advantage often sought, enables the natural defenses against ultraviolet radiation to be strengthened by increasing the proportion of melanin in the epidermis. These compositions can also be used, for example in the form of creams, to give the skin a more sunburnt appearance, or else in the form of lotions to prevent and treat the appearance of gray hair. Furthermore, the compositions according to the present invention can be used in dermatology as therapeutic agents, by themselves or in association with other drugs, in particular by topical administration in the treatment of melanogenesis dysfunctions.

Advantageously, the cosmetic or pharmaceutical compositions according to the invention which are intended for topical administration contain at least one agent for promoting penetration and diffusion in the cutaneous structures in question, such as the agents commonly used in the fields of cosmetology and dermopharmacy, for example glycerol, propylene glycol, oleic acid or essential oils, especially menthol and eucalyptol.

In one advantageous embodiment, a cosmetic or pharmaceutical composition according to the invention also contains a xanthine, in particular 1-methylxanthine, 3-methylxanthine, 3-isobutylmethylxanthine (IBMX) or theophylline, preferably at a concentration by weight of between 0.001% and 2% and particularly preferably of between 0.01% and 0.5%, based on the total weight of the composition.

In another embodiment, a cosmetic or pharmaceutical composition according to the invention also contains tyrosine or one of its derivatives, preferably at a concentration by weight of between 0.001% and 10%, based on the total weight of the composition.

In yet another embodiment, a cosmetic or pharmaceutical composition according to the invention also contains an effective concentration of at least one other active substance selected from vitamins, in particular the B vitamins, quinine or its derivatives, rubefacients such as methyl nicotinate, a papilla fibroblast culture supernatant as defined in the document EP-A-272 920, keratin hydrolyzates, trace elements such as zinc, selenium and copper, 5-α-reductase inhibitors such as progesterone, cyproterone acetate and minoxidil, azelaic acid and its derivatives, a 4-methyl- 4-azasteroid, in particular 17-β-N,N-diethyl-carbamoyl- 4-methyl-4-aza-5-α-androstan-3-one, or else an extract of Serenoa repens.

In yet another embodiment, a cosmetic or pharmaceutical composition according to the invention also contains hydrated lipidic lamellar phases or liposomes, which may or may not incorporate the extract of Cyperus defined above.

According to a second feature, the present invention further relates to a process for the manufacture of a cosmetic or pharmaceutical composition, especially dermatological composition, intended for promoting the pigmentation of the skin or hair, said process comprising the incorporation of at least one extract of Cyperus, as defined above, into a cosmetically or pharmaceutically acceptable excipient, vehicle or carrier.

According to a third feature, the invention relates to the use of an extract of Cyperus for the preparation of a cosmetic or pharmaceutical composition, especially dermatological composition, intended for promoting the pigmentation of the skin or hair and/or for treating disorders of the pigmentation of the skin and hair, as defined above.

Finally, according to a last feature, the present invention further relates to a method of treating the skin or hair in order to promote the pigmentation, said method comprising the application, in an amount effective for achieving pigmentation, of at least one extract of Cyperus as defined above, incorporated in a cosmetically or pharmaceutically acceptable excipient, vehicle or carrier.

In all the foregoing features of the present invention, provision can be made for the presence of hydrated lipidic lamellar phases or liposomes, which may or may not incorporate the above-mentioned extract of Cyperus.

The term "lipidic" in the expression "lipidic lamellar phase" covers all substances which comprise a so-called fatty hydrocarbon chain generally containing more than 5 carbon atoms, this substance usually being called a "lipid".

According to the invention, the lipids used to form the lipidic lamellar phases or the liposomes are amphiphilic lipids, i.e. lipids consisting of molecular which possess either an ionic or a non-ionic hydrophilic group and a lipophilic group, these amphiphilic lipids being capable of forming lipidic lamellar phases or liposomes in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an egg or soya lecithin, a phosphatidylserine, a sphyngomyelin, a cerebroside or an oxyethylenated polyglycerol stearate.

It is preferable according to the invention to use a mixture of lipids consisting of at least one amphiphilic lipid and at least one hydrophobic lipid such as a sterol like cholesterol or β-sitosterol. The amount of hydrophobic lipid, expressed in mol, must not generally exceed the amount of amphiphilic lipid and preferably must not exceed 0.5 times this amount.

The compounds or the extracts containing these compounds used according to the present invention can be incorporated into hydrated lipidic lamellar phases or into liposomes by known preparative techniques described for example in the document EP-B1-0 087 993, if appropriate in combination with the document EP-B1- 0 107 559.

Other objects, characteristics and advantages of the invention will become clearly apparent from the following explanatory description referring to several Examples, which are given solely by way of illustration and consequently cannot in any way limit the scope of the invention.

The percentages are given by weight in the Examples, unless indicated otherwise.

EXAMPLE 1

Preparation of an extract of *Cyperus rotundus L.*

500 g of tubers of *Cyperus rotundus L.* are treated under reflux for 3 h with a sufficient amount of methanol to completely immerse the plant material.

The methanolic extracts are filtered and the methanolic filtrate is evaporated under reduced pressure and then lyophilized to give the extract of tubers of *Cyperus rotundus* called extract $I_1$.

EXAMPLE 2

An extract of *Cyperus rotundus* called extract $I_2$ is obtained by following the procedure described in Example 1, except that the whole plant is used and ethyl acetate is used as the solvent.

EXAMPLE 3

Incorporation of an extract of tubers of *Cyperus rotundus* into hydrated lipidic lamellar phases or into liposomes An extract of tubers of *Cyperus rotundus* obtained according to Example 1 is incorporated into hydrated lipidic lamellar phases or into liposomes by the following preparative technique:

The following are weighed out:

soya lecithin: 1.8 g

β-sitosterol: 0.2 g lyophilized extract of Cyperus $I_1$ of Example 1: 0.03 g

These constituents are dissolved in a mixture made up of 25 ml of dichloromethane and 10 ml of methanol.

The resulting mixture is evaporated on a rotary evaporator at a temperature of 60° C. under reduced pressure.

The resulting lipidic film is then taken up and dispersed in distilled water qsp 50 g at room temperature for 12 h, with agitation.

The suspension of lipidic vesicles obtained is then homogenized by treatment with ultrasound for 10 min at 4° C., at a power of 150 W.

The resulting liposomes have a mean size of about 140 nm.

In one advantageous variant, this suspension is then gelled by being mixed with 50 g of 1.25% Carbopol® 940 gel, separately prepared in conventional manner. This gives about 100 g of a gelled suspension of liposomes encapsulating the extract of *Cyperus rotundus*, the concentration of which is about 0.030%, based on the total weight of the suspension.

EXAMPLE 4

Measurement of the activity of an extract of *Cyperus rotundus* L. according to the invention on melanocytes in culture

Protocol

S91 murine melanocytes, inoculated at a rate of $2 \cdot 10^5$ cells per dish, are cultivated in conventional manner on an appropriate medium comprising complemented EMEM, 1% of fetal calf serum and 0.08 μg of mitomycin C. 24 h after inoculation, the test product, diluted in DMSO and incorporated in fresh medium, is introduced into the culture.

After 5 d, the cells are removed and isolated by centrifugation and the cellular residue is recovered and dissolved in 0.5N sodium hydroxide.

The optical density is read on a spectrophotometer at 405 nm, which makes it possible to evaluate the amount of melanin formed by comparison with the optical density of a solution of melanin of known concentration.

The cells are also counted and the amount of melanin formed per cell is calculated.

An extract of *Cyperus rotundus* was tested, at various concentrations in μg/ml, using as positive control a culture receiving β-MSH (melanocyte-stimulating hormone) at a concentration of $2 \cdot 10^8 M$.

The melanogenesis-stimulating activity A of the products according to the invention is calculated by means of the following formula:

$$A = \frac{q_p - q_o}{q_t - q_o} \times 100$$

in which the quantities q represent the amounts of melanin formed:

$q_p$=culture receiving the test product $q_t$=culture receiving β-MSH $q_o$=control culture receiving no product The activity of the extract tested at different concentrations, calculated according to the above formula, is shown in Table I below.

TABLE I

Extract of *Cyperus rotundus* L. (Example 1)

| Concentration of product, μg/ml | Number of cells per dish × $10^3$ | Melanin, μg per $10^6$ cells | Activity % | t |
|---|---|---|---|---|
| Control (DMSO, no product) | 152 ± 8 | 65 ± 1 | 0 | |
| β-MSH at $2 \cdot 10^{-8}$ M | 158 ± 5 | 149 ± 3 | 100 | |
| 2.5 | 147 ± 3 | 71 ± 4 | +8 | NS |
| 10 | 148 ± 7 | 84 ± 0 | +25 | S |
| 25 | 147 ± 7 | 94 ± 3 | +38 | S |
| 50 | 155 ± 8 | 96 ± 3 | +41 | S |

Table I above shows that the extract of Cyperus according to the invention stimulates the production of melanin to a significant extent, representing a totally unexpected result for those skilled in the art.

Various Examples of the formulation of a cosmetic or pharmaceutical composition, especially dermatological composition, are given below.

EXAMPLE 5

Tanning Gel for the Face

| | |
|---|---|
| Extract of Cyperus (dry weight) according to Example 1 | 0.1 g |
| Ethanol | 40.— g |
| Distilled water | 20.— g |
| 1% Carbopol ® 940 gel qsp | 100 g |

EXAMPLE 6

Tanning Sun Cream

| | |
|---|---|
| Extract of Cyperus (dry weight) according to Example 1 | 0.02 g |
| Isocetyl stearate | 8.— g |
| Hydrogenated groundnut oil | 10.— g |
| Lanolin oil | 3.5 g |

-continued

| | |
|---|---|
| Cetyl alcohol | 5.— g |
| Stearyl alcohol | 2.5 g |
| Light liquid paraffin | 10.— g |
| Neutralized phosphoric acid monoester of oxyethylenated cetyl alcohol | 3.— g |
| Octylmethoxy cinnamate | 5.— g |

This phase is emulsified with an aqueous phase qsp 100 g containing:

| | |
|---|---|
| Pantothenol | 0.1 g |
| Preservatives | 0.2 g |

EXAMPLE 7

Lotion for Strengthening Natural Sun Protection

| | |
|---|---|
| Alcohol | 42.5 g |
| Propylene glycol | 3.— g |
| Menthol | 0.05 g |
| Hydroxypropyl methyl cellulose | 1.5 9 |
| Extract of Cyperus according to Example 1 | 0.03 g |
| Perfumed aqueous excipients qsp | 100 g |

This lotion is applied locally, preferably twice a day, every day for 3 to 8 days preceding prolonged exposure to the sun.

The daily applications can be continued during the period of exposure.

EXAMPLE 8

Hair Tonic Lotion for Combating Gray Hair

| | |
|---|---|
| Extract of Cyperus according to Example 2 | 0.01 g |
| 3-Methylxanthine | 0.03 g |
| Alcohol | 30.— g |
| Perfumed aqueous excipients with perfume qsp solubilizer | 100 g |

This lotion can be applied to the hair and scalp twice a day in three-month courses of treatment.

EXAMPLE 9

Hair Tonic Lotion for Combating Gray Hair

| | |
|---|---|
| Extract of *Cyperus rotundus* according to Example 1 | 1.0 g |
| Propylene glycol | 5.0 g |
| Perfume solubilizer (Crémophor RH 40 ®) | 0.5 g |
| Ethanol | 35.0 g |
| Perfumed aqueous excipients qsp | 100 g |

This lotion can be applied to the hair and scalp twice a day for a vigorous treatment intended for rapidly reducing the appearance of white hair.

EXAMPLE 10

Dermatological Gel Intended for Promoting the Pigmentation of the Skin

| | |
|---|---|
| Extract of Cyperus according to Example 1 | 0.1 g |
| Ethanol | 35.0 g |
| Distilled water | 15.0 g |
| Gelling excipient, for example 1.25% qsp Carbopol 940 ® gel | 100 g |

This gel is used once or twice a day by local application to the areas of skin to be treated.

EXAMPLE 11

Hair Lotion for Combating Gray Hair

| | |
|---|---|
| Extract of Cyperus according to Example 1 | 0.03 g |
| L-Tyrosine ethyl ester · HCl | 1.0 g |
| Ethanol | 40.0 g |
| Perfumed aqueous excipient with perfume qsp solubilizer | 100 g |

This lotion, applied daily to the hair and scalp, makes it possible to delay the appearance of gray hair.

EXAMPLE 12

Tanning Gel

| | |
|---|---|
| Extract of Cyperus according to Example 1 | 0.02 g |
| Sun filter (EUSOLEX 232 TS ®) | 8.0 g |
| Ethanol | 40.0 g |
| Gelling excipient (comprising: 1.25% qsp Carbopol 940 ®) | 100 g |

EXAMPLE 13

Lotion for Preventing the Appearance of Gray Hair

| | |
|---|---|
| Suspension of liposomes encapsulating an extract of Cyperus, according to Example 3 | 50 g |
| Carbopol 940 ® | 0.05 g |
| Glucose tyrosinate | 0.05 g |
| Trace element complex | 0.1 g |
| Theophylline | 0.01 g |
| Preservative | 0.05 g |
| Aqueous excipient, for example distilled water qsp | 100 ml |

This solution is applied in the evening to the graying areas of the scalp in a 4-month course of treatment.

EXAMPLE 14

Body Lotion

| | |
|---|---|
| Extract of *Cyperus rotundus* according to Example 1 | 0.01 g |
| N-Malyltyrosine | 1.00 g |

-continued

| Propylene glycol | 3.00 g |
| --- | --- |
| Perfumed aqueous excipients with solubilizer qsp | 100.00 g |

Of course, the invention embraces all the means which constitute technical equivalents of the means described, as well as the various combinations thereof.

What is claimed is:

1. A method of treatment of skin or hair for promoting the pigmentation, comprising applying a pigmenting effective amount of at least one Cyperus extract to a person in need of skin or hair pigmentation by promoting melanogenesis.

2. The method of claim 1, wherein said Cyperus extract is incorporated in a cosmetically or pharmaceutically acceptable excipient.

3. The method of claim 1, wherein said Cyperus extract is an organic extract of Cyperus obtained by a process comprising at least one extracting step with a solvent.

4. The method of claim 3, wherein said solvent is an organic solvent selected from the group consisting of a aromatic hydrocarbon, a aliphatic hydrocarbon, a halogenated aliphatic hydrocarbon, a halogenated aromatic hydrocarbon, a dialkyl ether, a dialkyl ketone, an alkanol, a carboxylic acid, a carboxylic acid ester, dimethylformamide, dioxane, tetrahydrofuran and dimethyl sulfoxide, and a hydroalcoholic solvent.

5. The method of claim 1, wherein said solvent is selected from the group consisting of benzene, toluene, xylene, methylene chloride, chloroform, ethyl acetate, methanol, ethanol and a hydroalcoholic solvent.

6. The method of claim 1, wherein said Cyperus extract is an organic extract of Cyperus obtained by a process comprising at least one extracting step with a solvent selected from the group consisting of methanol, ethanol, a hydroalcoholic admixture with methanol, a hydroalcoholic mixture with ethanol, dichloromethane and ethyl acetate.

7. The method of claim 1, wherein the concentration in Cyperus extract, expressed in dry weight, is ranging between 0.002% and 5% by weight.

8. The method of claim 1, wherein the concentration in Cyperus extract, expressed in dry weight, ranges between 0.01% and 1% by weight.

9. The method of claim 1, wherein said Cyperus extract is applied in admixture with at least one xanthine.

10. The method of claim 9, wherein said xanthine is selected from the group consisting of 1-methyl xanthine, 3-methyl xanthine, isobutylmethyl xanthine and theophylline.

11. The method of claim 9, wherein said xanthine is present at a concentration ranging between 0.001% and 2% by weight.

12. The method of claim 1, wherein said Cyperus extract is present in admixture with a tyrosine component selected from tyrosine and a tyrosine derivative.

13. The method of claim 12, wherein said tyrosine component is present at a concentration ranging between 0.001% and 10% by weight.

14. The method of claim 1, wherein said Cyperus extract is present in admixture with a lipidic component selected from lipidic lamellar phases and liposomes.

15. The method of claim 14, wherein the liposomes contain said Cyperus extract.

16. The method of claim 1, wherein said Cyperus extract is present in a composition formulated in a form appropriate for a topical application on the skin or the hair.

17. The method of claim 16, wherein said composition is under a form selected from the group consisting of a cream, a gel or a lotion.

18. The method of claim 1, wherein said Cyperus extract is applied in admixture with at least one agent promoting penetration and diffusion in the cutaneous structures.

19. The method of claim 18, wherein said penetration and diffusion promoting agent is selected from the group consisting of glycerol, propylene glycol, oleic acid and an essential oil.

20. The method according to claim 1, wherein said Cyperus extract is present in a composition formulated as a dermatological composition.

21. The method according to claim 1, wherein said Cyperus extract is present in a composition formulated as a sun product to accelerate or intensify tanning or prevent and treat the appearance of gray hair.

22. The method of claim 1, wherein said Cyperus extract is present in admixture with an efficient amount of an active substance selected from the group of a vitamin, quinine, quinine derivatives, a rubefacient, a 5-α-reductase inhibitor, ciproterone acetate, minoxidil, azelaic acid, an azelaic acid derivative, a 4-methyl- 4-azasteroid, and an extract of Serenoa repens.

* * * * *